United States Patent [19]

Alt

[11] Patent Number: 4,606,759

[45] Date of Patent: Aug. 19, 1986

[54] HERBICIDAL 2-HALOACETANILIDES

[75] Inventor: Gerhard H. Alt, University City, Mo.

[73] Assignee: Monsanto Company, St. Louis, Mo.

[21] Appl. No.: 237,193

[22] Filed: Feb. 23, 1981

Related U.S. Application Data

[63] Continuation-in-part of Ser. No. 134,034, Mar. 25, 1980, abandoned.

[51] Int. Cl.[4] ..................... A01N 37/22; C07C 103/32
[52] U.S. Cl. .......................................... 71/118; 71/76; 564/214
[58] Field of Search ........................... 71/118; 564/214

[56] References Cited

U.S. PATENT DOCUMENTS 3,442,945 5/1969 Olin ................................. 260/562 B
3,547,620 12/1970 Olin ....................................... 71/118
4,152,137 5/1979 Martin ................................... 71/118

FOREIGN PATENT DOCUMENTS 810763 2/1974 Belgium .
2402983 8/1974 Fed. Rep. of Germany .

*Primary Examiner*—Catherine L. Mills
*Attorney, Agent, or Firm*—William I. Andress; Robert B. Martin

[57] ABSTRACT

The disclosure herein relates to a group of N-alkoxymethyl-2-haloacetanilide compounds, herbicidal compositions containing said compounds as the active ingredient and herbicidal method of use in various crops, particularly sorghum. Herbicides herein are particularly effective against hard-to-control weeds particularly seedling johnsongrass and/or shattercane, white proso millet, yellow nutsedge and redroot pigweed in addition to yellow foxtail, barnyardgrass and crabgrass.

27 Claims, No Drawings

1

HERBICIDAL 2-HALOACETANILIDES

BACKGROUND OF THE INVENTION

CROSS-REFERENCE TO RELATED APPLICATION

This application is a continuation-in-part of U.S. application Ser. No. 134,034, filed Mar. 25, 1980, abandoned.

FIELD OF THE INVENTION

This invention pertains to the field of 2-haloacetanilides and their use in the agronomic arts, e.g., as herbicides.

DESCRIPTION OF THE PRIOR ART

The prior art relevant to this invention includes numerous disclosures of 2-haloacetanilides which may be unsubstituted or substituted with a wide variety of substituents on the anilide nitrogen atom and on the anilide ring including alkyl, alkoxy, alkoxyalkyl, halogen, etc., radicals.

As relevant to the invention compounds, which are characterized by having an alkoxymethyl or alkenyloxymethyl radical on the anilide nitrogen, an alkoxy or alkenyloxy radical in one ortho position and hydrogen or a specific alkyl radical in the other ortho position, the closest prior art known to the inventor are U.S. Pat. Nos. 3,442,945 and 3,547,620. The most relevant disclosures in the '945 and '620 patents are the compounds 2'-tert-butyl-2-chloro-N-methoxymethyl-6'-methoxyacetanilide and its bromo analog (Examples 18 and 34 of the '620 patent and Examples 18 and 36 of the '945 patent, respectively).

U.S. Pat. Nos. 4,070,389 and 4,152,137 disclose a generic formula which encompasses compounds of the type disclosed in said '945 and '620 patents. However, the only disclosed species compound having an alkyl radical in one ortho position and an alkoxy radical in the other ortho position has an alkoxyethyl radical on the anilide nitrogen atom; compounds of this type are discussed in more detail below.

Other less-relevant prior art are Belgian Pat. No. 810,763 and German application No. 2,402,983; the compounds of these references include compounds of the type disclosed in said '389 and '137 patents and are characterized by an alkoxyalkyl radical having two or more carbon atoms between the anilide nitrogen atom and the oxygen atom of the alkoxy moiety. The most relevant specific disclosures in said Belgian '763 patent and German '983 application appear to be compounds having an ethoxyethyl radical on the anilide nitrogen atom, a methoxy or ethoxy radical in one ortho position and a methyl or isopropyl radical in the other ortho position. Referring to the '763 patent, see Compound Numbers 7, 16 and 18; other less-relevant homologs of these compounds are also disclosed, e.g., Compounds 6, 9 and 17, which have methoxyethyl or methoxypropyl radicals substituted on the nitrogen atom and a methoxy or ethoxy radical in one ortho position and a methyl or ethoxy radical in the other ortho position.

The above '945 patent which discloses those above-mentioned compounds having a chemical configuration most closely related to the invention compounds contain some herbicidal data therefore, and some data are presented for other homologous and analogous compounds less-closely related in chemical structure. Similarly, some data is presented for said Compound Numbers 6 and 9 in said Belgian Pat. No. 810,763. More particularly, these most relevant references, while disclosing herbicidal activity on a variety of weeds, do not disclose any data for any compounds which are shown to additionally and/or simultaneously control the hard-to-control narrowleaf weeds, seedling johnsongrass and/or shattercane, both of which belong to the same plant genus as sorghum, and other hard-to-kill weeds such as redroot pigweed and wild proso millet, in addition to less-resistant weeds such as yellow foxtail, barnyardgrass and crabgrass, while maintaining safety to sorghum. Said Belgian '763 patent presents data showing that Compound No. 6 destroys sorghum, while no data is presented for the effect of Compound No. 9 on sorghum. As will be shown herein, the novel compounds of this invention possess unexpectedly superior properties as selective herbicides in sorghum vis-a-vis the homologous compounds of the prior art.

It is an object of this invention to provide herbicides which selectively control hard-to-control weeds such as seedling johnsongrass and/or shattercane and for certain species of this invention other hard-to-kill weeds such as redroot, pigweed and wild proso millet, in addition to less-resistant weeds such as yellow foxtail, barnyardgrass and crabgrass, particularly in sorghum, in a manner superior to that of prior art.

The above and other objects of the invention will become more apparent from the detailed description below.

SUMMARY OF THE INVENTION

The present invention relates to herbicidally active compounds, herbicidal compositions containing these compounds as active ingredients and herbicidal method of use of said compositions in particular crops, especially sorghum.

It has now been found that a selective group of 2-haloacetanilides characterized by specific alkoxymethyl or alkenyloxymethyl radicals on the anilide nitrogen atom, specific alkoxy radicals in one ortho position and hydrogen or the methyl radical in the other ortho position possess unexpectedly superior and outstanding selective herbicidal properties as sorghum herbicides vis-a-vis prior art herbicides, including homologous compounds of the most relevant prior art.

A primary feature of the herbicidal compositions of this invention is their ability to selectively control narrowleaf weeds, seedling johnsongrass and/or shattercane which are species of the same plant genus as sorghum; in fact, sorghum and shattercane are both sorghum bicolor species. Hence, it is exceedingly difficult to selectively control shattercane and seedling johnsongrass in sorghum without simultaneously injuring the sorghum. Additionally, some members of the invention compounds also control other hard-to-kill species such as redroot pigweed, yellow nutsedge and/or white proso millet and all invention compounds control other species such as yellow foxtail, barnyardgrass, crabgrass and other noxious weeds.

The compounds of this invention are characterized by the formula

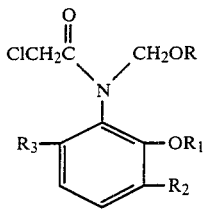

wherein

R is isopropyl, isopropyl, n-butyl, isobutyl, sec-butyl, allyl or 2-methylbutyl;

$R_1$ is methyl, isopropyl, n-butyl or allyl and $R_2$ and $R_3$ are hydrogen or methyl; provided that:

$R_1$, $R_2$ and $R_3$ are each methyl when R is n-butyl, isobutyl or sec-butyl;

$R_2$ and $R_3$ are each hydrogen when R is isopropyl, isobutyl or sec-butyl and $R_1$ is isopropyl or n-butyl and $R_2$ is hydrogen and $R_3$ is methyl when R is 2-methylbutyl or allyl and $R_1$ is allyl.

Preferred species of compounds of this invention are:

N-(isobutoxymethyl)-2'-methoxy-3',6'-dimethyl-2-chloroacetanilide,

N-(n-butoxymethyl)-2'-methoxy-3',6'-dimethyl-2-chloroacetanilide,

N-(sec-butoxymethyl)-2'-methoxy-3',6'-dimethyl 1-2-chloroacetanilide,

N-(allyloxymethyl)-2'-allyloxy-6-methyl-2-chloroacetanilide,

N-(2-methylbutoxymethyl)-2'-allyl-6'-methyl-2-chloroacetanilide,

N-(isopropoxymethyl)-2'-isopropoxy-2-chloroacetanilide,

N-(isobutoxymethyl)-2'-isopropoxy-2-chloroacetanilide and

N-(sec-butoxymethyl)-2'-n-butoxy-2-chloroacetanilide.

The utility of the compounds of this invention as the active ingredient in herbicidal compositions formulated therewith and the method of use thereof will be described below.

DETAILED DESCRIPTION OF THE INVENTION

The compounds of this invention may be made in a variety of ways. For example, these compounds may be prepared by the azomethine route described in the above-mentioned U.S. Pat. Nos. 3,442,945 and 3,547,620. According to the azomethine process, the appropriate primary aniline is reacted with formaldehyde to obtain the corresponding methyleneaniline (substituted phenylazomethine), which is then reacted with a haloacetylating agent such as chloroacetyl chloride or chloroacetyl anhydride which, in turn, is reacted with the appropriate alcohol to obtain the corresponding N-alkoxymethyl- or N-alkenyloxymethyl-2-chloroacetanilide as the final product.

Another process for producing compounds according to this invention involves an N-alkylation of the anion of the appropriate secondary 2-haloacetanilide with an alkylating agent under basic conditions. The N-alkylation process is described in more detail in copending U.S. Ser. No. 63,005, filed Aug. 2, 1979, assigned to the same assignee herein. A modification of said N-alkylation process is described in Example 1 for preparing the compounds of this invention. The N-alkylation process described in Example 1 herein involves the in situ preparation of halomethyl alkyl ethers used as starting materials in the N-alkylation process. The in situ process is the invention of other employees of the assignee of the present application and is described in greater detail in U.S. Ser. No. 133,720, filed Mar. 25, 1980 and titled, "A process For The In-Solvent, In Situ Generation of Haloalkyl Ethers Useful To Produce N-Substituted-2-Haloacetanilides", inventors Chupp and Alt.

EXAMPLE 1

This example describes the use of an N-alkylation process to prepare compounds according to this invention. In the process embodiment of this example, the alkylating agent is formed in situ, thus effecting an efficient, economic and simple operation.

To a chilled mixture of 9.25 g (0.125 mol) of isobutanol, 1.86 g (0.062 mol) of anhydrous paraformaldehyde and 100 ml of methylene chloride was added 7.56 g (0.062 mol) of acetyl bromide; the mixture was stirred until all the paraformaldehyde was dissolved, i.e., about 45 minutes. To the mixture was then added 4.55 g (0.02 mol) of 2'-methoxy-3',6'-dimethyl-2-chloroacetanilide, and 2.0 g of benzyl triethylammonium chloride in 100 ml of methylene chloride. The mixture was cooled to 15° C. and 50 ml of 50% NaOH added all at once and stirred for 5 minutes. To the mixture was added 150 ml of cold water. The layers were separated, washed with water, dried over $MgSO_4$ and evaporated by Kugelrohr to obtain 5.0 g (79% yield) of yellow liquid, b.p. 107° C. at 0.02 mm Hg.

Anal. Calc'd for $C_{16}H_{24}ClNO_3$ (%): C, 61.24; H, 7.71; Cl, 11.30 Found: C, 61.24; H, 7.72; Cl, 11.28

The product was identified as N-(isobutoxymethyl)-2'-methoxy-3',6'-dimethyl-2-chloroacetanilide.

EXAMPLES 2–8

Following substantially the same procedure and conditions described in Examples 1, but substituting the appropriate secondary anilide and alkylating agent as starting materials and quantities thereof, the corresponding N-(alkoxymethyl) and N-(alkenyloxymethyl)-2-haloacetanilides were prepared; these compounds are identified in Table I, together with certain physical properties.

TABLE I

| Example No. | Compound | Emperical Formula | B.P. °C. (mm Hg) | Element | Analysis Calculated | Found |
|---|---|---|---|---|---|---|
| 2 | N—(isopropoxymethyl)-2'-isopropoxy-2-chloroacetanilide | $C_{15}H_{22}ClNO_3$ | 113 (0.01) | C H Cl | 60.10 7.40 11.83 | 60.38 6.80 11.94 |
| 3 | N—(isobutoxymethyl)-2'-isopropoxy-2-chloroacetanilide | $C_{16}H_{24}ClNO_3$ | 113 (0.03) | C H Cl | 61.24 7.71 11.30 | 61.23 7.72 11.30 |
| 4 | N—(allyloxymethyl)-2'-allyloxy-6'-methyl-2-chloroacetanilide | $C_{16}H_{20}ClNO_3$ | 116 (0.03) | C H | 62.03 6.51 | 61.98 6.53 |

TABLE I-continued

| Example No. | Compound | Emperical Formula | B.P. °C. (mm Hg) | Element | Analysis Calculated | Found |
|---|---|---|---|---|---|---|
| | | | | Cl | 11.44 | 11.44 |
| 5 | N—(sec-butoxymethyl)-2'-n-butyl-2-chloroacetanilide | $C_{17}H_{26}ClNO_3$ | 115 (0.02) | C | 62.28 | 62.18 |
| | | | | H | 7.99 | 8.03 |
| | | | | Cl | 10.81 | 10.80 |
| 6 | N—(n-butoxymethyl)-2'-methoxy-3',6'-dimethyl-2-chloroacetanilide | $C_{16}H_{25}ClNO_3$ | 108 (0.1) | C | 61.24 | 61.15 |
| | | | | H | 7.71 | 7.79 |
| | | | | Cl | 11.30 | 11.30 |
| 7 | N—(sec-butoxymethyl)-2'-methoxy-3'-6'-dimethyl-2-chloroacetanilide | $C_{16}H_{24}ClNO_3$ | 116 (0.07) | C | 61.24 | 61.13 |
| | | | | H | 7.71 | 7.78 |
| | | | | Cl | 11.30 | 11.24 |
| 8 | N—(2-methylbutoxymethyl)-2'-allyl-6'-methyl-2-chloroacetanilide | $C_{18}H_{26}ClNO_3$ | 118 (0.08) | C | 63.61 | 63.61 |
| | | | | H | 7.71 | 7.79 |
| | | | | Cl | 10.43 | 10.44 |

The secondary anilide starting materials used in the preparation of the above examples are prepared according to known methods, e.g., by haloacetylation of the corresponding primary amine with such haloacetylation agents as a haloacetyl halide or anhydride. Typically, the appropriate quantity of the appropriate primary amine is dissolved in a solvent such as methylene chloride containing a base, e.g., 10% NaOH, and stirred vigorously while mixing with a solution of the haloacetyl halide, e.g., chloroacetyl chloride, under external cooling, e.g., at 15°-25° C. The layers are separated and the organic solvent layer washed with water, dried and evaporated in vacuo.

The primary amines used to prepare the secondary anilides also may be prepared by known means, e.g., by catalytic reduction of the corresponding appropriately-substituted nitrobenzene, e.g., 2-alkoxy-6-alkyl nitrobenzene, in a solvent such as an alcohol, e.g., ethanol, using platinum oxide catalyst; for 2-alkenyloxy (e.g., allyloxy)-6'-alkyl compounds, a chemical reduction using iron and acetic acid may be used.

As noted above, the compounds of this invention have been found to be effective as herbicides, particularly as pre-emergence herbicides, although post-emergence activity has also been shown. Tables II and III summarize results of tests conducted to determine the pre-emergent herbicidal activity of the compounds of this invention.

The pre-emergent test was conducted as follows:

A good grade of top soil is placed in aluminum pans and compacted to a depth of three-eighths to one-half inch from the top of the pan. On the top of the soil is placed a predetermined number of seeds or vegetative propagules of various plant species. The soil required to level fill the pans after seeding or adding vegetative propagules is weighed into a pan. The soil and a known amount of the active ingredient applied in a solvent or as a wettable powder suspension are thoroughly mixed, and used to cover the prepared pans. After treatment, the pans are moved into a greenhouse bench where they are given an initial overhead irrigation of water, equivalent to one-fourth inch (0.64 cm) rainfall, then watered by subirrigation as needed to give adequate moisture for germination and growth.

Approximately 2 weeks aftr seeding and treating, the plants were observed and the results recorded. Tables II and III below, summarize such results. The herbicidal rating was obtained by means of a fixed scale based on the percent injury of each plant species. The ratings are defind as follows:

| % Control | Rating |
|---|---|
| 0-24 | 0 |
| 25-49 | 1 |
| 50-74 | 2 |
| 75-100 | 3 |

The plant species utilized in one set of tests, the data for which are shown in Table II, are identified by letter in accordance with the following legend:

| A | Canada Thistle | E | Lambsquarters | I | Seedling Johnsongrass |
|---|---|---|---|---|---|
| B | Cocklebur | F | Smartweed | | |
| C | Velvetleaf | G | Yellow Nutsedge | J | Downy Brome |
| D | Morningglory | H | Quackgrass | K | Barnyardgrass |

TABLE II

| Compound of Example | | Pre-Emergent Plant Species | | | | | | | | | | |
|---|---|---|---|---|---|---|---|---|---|---|---|---|
| No. | kg/h | A | B | C | D | E | F | G | H | I | J | K |
| 1 | 11.2 | 3 | 3 | 0 | 3 | 3 | 3 | 3 | 3 | 0 | 3 | 3 |
| | 5.6 | 1 | 1 | 0 | 3 | 2 | 3 | 3 | 3 | 0 | 3 | 3 |
| 2 | 11.2 | 0 | 1 | 1 | 3 | 1 | 1 | 0 | 3 | 0 | 3 | 3 |
| | 5.6 | 0 | 0 | 1 | 2 | 0 | 1 | 0 | 0 | 0 | 3 | 3 |
| 3 | 11.2 | 3 | 0 | 1 | 1 | 0 | 2 | 3 | 2 | 0 | 3 | 3 |
| | 5.6 | 0 | 0 | 1 | 1 | 0 | 1 | 3 | 0 | 0 | 3 | 3 |
| 4 | 11.2 | 3 | 1 | 2 | 2 | 2 | 2 | 3 | 0 | 3 | 3 | 3 |
| | 5.6 | 3 | 1 | 1 | 1 | 3 | 2 | 3 | 3 | 3 | 3 | 3 |
| 5 | 11.2 | — | — | — | — | 2 | 2 | 3 | 2 | 1 | 3 | 3 |
| | 5.6 | 0 | 0 | 0 | 0 | 0 | 1 | 3 | 1 | 0 | 3 | 3 |
| 6 | 11.2 | 3 | 2 | 1 | 2 | 3 | 3 | 3 | 3 | 3 | 3 | 3 |
| | 5.6 | 3 | 2 | 1 | 2 | 3 | 3 | 3 | 2 | 0 | 3 | 3 |
| 7 | 11.2 | 3 | 2 | 1 | 2 | 3 | 3 | 3 | 3 | 3 | 3 | 3 |
| | 5.6 | 3 | 1 | 1 | 2 | 2 | 3 | 3 | 3 | 1 | 3 | 3 |
| 8 | 11.2 | 3 | 0 | 0 | 0 | 2 | 3 | 1 | 2 | 1 | 3 | 3 |
| | 5.6 | 0 | 0 | 0 | 0 | 0 | 0 | 1 | 2 | 2 | 3 | 3 |

The compounds were further tested by utilizing the above procedure on the following plant species:

| L | Soybean | R | Hemp Sesbania |
|---|---|---|---|
| M | Sugarbeet | E | Lambsquarters |
| N | Wheat | F | Smartweed |
| O | Rice | C | Velvetleaf |
| P | Sorghum | J | Downy Brome |
| B | Cocklebur | S | Panicum Spp. |
| Q | Wild Buckwheat | K | Barnyardgrass |
| D | Morningglory | T | Crabgrass |

The results are summarized in Table III.

TABLE III

Pre-Emergent

| Compound of Example No. | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- |
| 1 | 5.6 | 3 | 2 | 2 | 3 | 2 | 2 | 2 | 3 | 3 | 3 | 2 | 0 | 3 | 3 | 3 | 3 |
|   | 1.12 | 1 | 2 | 0 | 3 | 0 | 1 | 0 | 0 | 2 | 2 | 3 | 0 | 3 | 3 | 3 | 3 |
|   | 0.28 | 0 | 1 | 0 | 2 | 0 | 0 | 0 | 0 | 0 | 0 | 0 | 0 | 1 | 2 | 3 | 3 |
|   | 0.06 | 0 | 1 | 0 | 1 | 0 | 1 | 1 | 0 | 0 | 0 | 0 | 0 | 0 | 1 | 3 | 3 |
|   | 0.01 | 0 | 1 | 0 | 0 | 0 | 0 | 0 | 0 | — | 0 | 0 | 0 | 0 | 0 | 1 | 3 |
| 2 | 5.6 | 1 | 2 | 2 | 3 | 1 | 0 | 2 | 2 | 2 | 3 | 3 | 0 | 3 | 3 | 3 | 3 |
|   | 1.12 | 0 | 1 | 0 | 1 | 0 | 0 | 2 | 2 | 0 | 1 | 0 | 0 | 3 | 3 | 3 | 3 |
|   | 0.28 | 0 | 0 | 0 | 0 | 0 | 0 | 0 | 1 | 0 | 2 | 0 | 0 | 2 | 3 | 3 | 3 |
|   | 0.06 | 0 | 0 | 0 | 0 | 1 | 0 | 1 | 1 | 1 | 2 | 0 | 0 | 2 | 3 | 3 | 3 |
| 3 | 5.6 | 0 | 2 | 3 | 3 | 1 | 0 | 0 | 2 | 1 | 3 | 3 | 0 | 3 | 3 | 3 | 3 |
|   | 1.12 | 0 | 0 | 2 | 3 | 1 | 0 | 0 | 1 | 1 | 1 | 0 | 0 | 2 | 3 | 3 | 3 |
|   | 0.28 | 0 | 0 | 2 | 2 | 0 | 0 | 0 | 0 | 0 | 0 | 0 | 0 | 1 | 3 | 3 | 3 |
|   | 0.06 | 0 | 0 | 0 | 1 | 0 | 0 | 1 | 0 | 0 | 0 | 0 | 0 | 1 | 1 | 3 | 3 |
| 4 | 5.6 | 2 | 2 | 3 | 3 | 3 | 0 | 2 | 1 | 3 | 2 | 3 | 1 | 3 | 3 | 3 | 3 |
|   | 1.12 | 1 | 2 | 2 | 3 | 1 | 0 | 1 | 0 | 1 | 1 | 0 | 0 | 3 | 3 | 3 | 3 |
|   | 0.28 | 1 | 2 | 0 | 3 | 1 | 0 | 0 | 0 | 1 | 1 | 1 | 0 | 3 | 3 | 3 | 3 |
|   | 0.06 | 0 | 1 | 0 | 1 | 0 | 0 | 0 | 0 | 1 | 1 | 1 | 0 | 1 | 2 | 3 | 3 |
|   | 0.01 | 0 | 0 | 0 | 0 | 0 | 0 | 0 | 0 | 1 | 0 | 0 | 0 | 0 | 0 | 1 | 3 |
| 5 | 5.6 | 0 | 2 | 2 | 2 | 1 | 0 | 1 | 1 | 3 | 2 | 2 | 0 | 3 | 3 | 3 | — |
|   | 1.12 | 0 | 1 | 0 | 2 | 0 | 0 | 0 | 0 | 1 | 0 | 1 | 0 | 3 | 3 | 3 | — |
|   | 0.28 | 0 | 1 | 0 | 1 | 0 | 0 | 0 | 0 | 1 | 1 | 1 | 0 | 3 | 1 | 3 | — |
|   | 0.06 | 0 | 0 | 0 | 0 | 0 | 0 | 0 | 0 | 1 | 0 | 0 | 0 | 0 | 0 | 2 | — |
| 6 | 5.6 | 2 | 2 | 2 | 3 | 3 | 2 | 2 | 2 | 3 | 2 | 2 | 1 | 3 | 3 | 3 | — |
|   | 1.12 | 1 | 2 | 2 | 3 | 2 | 1 | 2 | 2 | 3 | 2 | 2 | 0 | 3 | 3 | 3 | — |
|   | 0.28 | 0 | 1 | 1 | 1 | 0 | 0 | 1 | 1 | 1 | 1 | 1 | 0 | 2 | 3 | 3 | — |
|   | 0.06 | 0 | 1 | 1 | 1 | 0 | 0 | 1 | 1 | 2 | 0 | 0 | 0 | 1 | 2 | 3 | — |
|   | 0.01 | 1 | 1 | 0 | 0 | 0 | 0 | 0 | 1 | 1 | 0 | 0 | 0 | 0 | 2 | 3 | — |
| 7 | 5.6 | 2 | 2 | 3 | 3 | 2 | 1 | 3 | 2 | 3 | 3 | 3 | 1 | 3 | 3 | 3 | — |
|   | 1.12 | 1 | 2 | 1 | 3 | 1 | 0 | 1 | 1 | 2 | 2 | 2 | 0 | 3 | 3 | 3 | — |
|   | 0.28 | 0 | 2 | 1 | 3 | 0 | 0 | 1 | 0 | 2 | 1 | 1 | 0 | 2 | 3 | 3 | — |
| 8 | 5.6 | 0 | 1 | 2 | 2 | 1 | 0 | 1 | 1 | 1 | 0 | 1 | 0 | 3 | 3 | 3 | — |
|   | 1.12 | 0 | 1 | 1 | 1 | 0 | 0 | 0 | 0 | 0 | 3 | 0 | 3 | 3 | 3 | 3 | — |
|   | 0.28 | 0 | 0 | 0 | 0 | 0 | 0 | 0 | 0 | 1 | 0 | 3 | 0 | 1 | 0 | 3 | — |
|   | 0.06 | 0 | 0 | 0 | 0 | 0 | 0 | 0 | 0 | 0 | 3 | 0 | 0 | 0 | 0 | 0 | — |
|   | 0.01 | 0 | 0 | 0 | 0 | 0 | 0 | 0 | 0 | 0 | 0 | 0 | 0 | 0 | 0 | 0 | — |

The herbicides of this invention have been found to possess unexpectedly superior properties as selective pre-emergence herbicides for use in sorghum, most particularly in the selective control of hard-to-kill weeds including one or more of the weeds seedling johnsongrass, shattercane, redroot pigweed, yellow nutsedge and white proso millet in addition to other problem weeds such as yellow foxtail, barnyardgrass and large crabgrass. Selective control and suppression of some of the above-mentioned and other weeds with the invention herbicides has been found in a variety of other crops including soybeans, wheat, rice and sugarbeet as indicated in Table II above. However, the markedly outstanding herbicidal properties of the invention compounds are most manifest in their selective control of weeds in sorghum.

In order to illustrate the unexpectedly superior properties of the compounds of this invention both on an absolute basis and on a relative basis, comparative tests were conducted in the greenhouse with: (1) homologous compounds of the prior art most closely related in chemical structure to the invention compounds and (2) two other compounds, which though not homologs, fall within the scope of said prior art and one of which has superior properties as a sorghum herbicide and both of which are commercial herbicides. All of the compounds in the comparative tests below are generically defined as substituted phenyl-N-hydrocarbyloxyalkyl-2-haloacetanilide. As used in the tables of data herein the compared prior art compounds are identified as follows:

A. N-(methoxymethyl)-2'-methoxy-6'-tert-butyl-2-chloroacetanilide. (Example 18, U.S. Pat. Nos. 3,442,945 and 3,547,620).

B. N-(methoxymethyl)1-2'-methoxy-6'-tert-butyl-2-bromoacetanilide. (Example 34 of said '620 patent and Example 36 of said '945 patent).

C. N-(methoxyethyl)-2'-methoxy-6'-methyl-2-chloroacetanilide. (Compound No. 6 of said Belgian '763 patent; also listed in German application No. 2,402,983).

D. n-(ethoxyethyl)-2'-methoxy-6'-methyl-2-chloroacetanilide. (Compound No. 7 in Belgian Pat. No. 810,763).

E. N-(1-methoxyprop-2-yl)-2'-methoxy-6'-methyl-chloroacetanilide. (Compound No. 9 of said Belgian '763 patent).

F. N-(methoxyethyl)-2'-ethoxy-6'-methyl-2-chloroacetanilide. (Compound No. 16 of said Belgian '763 patent).

G. N-(ethoxyethyl)-2'-ethoxy-6'-methyl-2-chloroacetanilide. (Compound No. 18 of said Belgian '763 patent).

H. N-isopropyl-2-chloroacetanilide; common name "propachlor".

I. N-(methoxymethyl)-2',6'-diethyl-2-chloroacetanilide. (Example 5 of said '620 and '945 patents); common name "alachlor", active ingredient in the commercial herbicide LASSO ®, registered trademark of Monsanto Company.

J. N-(isopropoxyethyl)-2'-methoxy-6'-methyl-2-chloroacetanilide.

Although Compound H above is less similar in structure than the mentioned homologous herbicides in said '945 and '620 patents, in that it lacks an alkoxyalkyl or alkenyloxy alkyl substituent on the nitrogen atom and an alkoxy substituent in an ortho position, it is included in tests herein because it is referred to in said '389 and '137 patents and has shown superior properties as a commercial sorghum herbicide vis-a-vis other compounds in said patents. Similarly, Compound I is included in tests herein because it is within the scope of the '945 and '620 patents and has achieved status as a commercial herbicide.

In pre-emergence herbicidal tests, compounds of this invention were compared with compounds A-J of the prior art with respect to control of various weeds, with emphasis on the hard-to-kill narrowleaf species which are prevalent infestations in sorghum. Test results are presented below.

In the discussion of data below, reference is made to herbicide application rates symbolized as "$GR_{15}$" and "$GR_{85}$"; these rates are given in kilograms per hectare (kg/ha) which are convertible into pounds per acre (lbs/A) by dividing the kg/ha rate by 1.12. $GR_{15}$ defines the maximum rate of herbicide required to produce 15% or less crop injury, and $GR_{85}$ defines the minimum rate required to achieve 85% inhibition of weeds. The $GR_{15}$ and $GR_{85}$ rates are used as a measure of potential commercial performance, it being understood, of course, that suitable commercial herbicides may exhibit greater or lesser plant injuries within reasonable limits.

A further guide to the effectiveness of a chemical as a selective herbicide is the "selectivity factor" ("SF") for a herbicide in given crops and weeds. The selectivity factor is a measure of the relative degree of crop safety and weed injury and is expressed in terms of the $GR_{15}/GR_{85}$ ratio, i.e., the $GR_{15}$ rate for the crop divided by the $GR_{85}$ rate for the weed, both rates in kg/ha (lb/A). In the tables below, where used, selectivity factors are shown in parenthesis following the weed; the symbol "NS" indicates "non-selective." Marginal or questionable selectivity is indicated by a dash (-) after the crop.

Since crop tolerance and weed control are interrelated, a brief discussion of this relationship in terms of selectivity factors is meaningful. In general, it is desirable that crop safety factors, i.e., herbicide tolerance values, be high, since higher concentrations of herbicide are frequently desired for one reason or another. Conversely, it is desirable that weed control rates be small, i.e., the herbicide possesses high unit activity, for economical and possibly ecological reasons. However, small rates of application of a herbicide may not be adequate to control certain weeds and a larger rate may be required. Hence the best herbicides are those which control the greatest number of weeds with the least amount of herbicide and provide the greatest degree of crop safety, i.e., crop tolerance. Accordingly, use is made of "selectivity factors" (defined above) to quantify the relationship between crop safety and weed control. With reference to the selectivity factors listed in the tables, the higher the numerical value, the greater selectivity of the herbicide for weed control in a given crop.

The preemergence tests referred to herein include both greenhouse and field tests. In the greenhouse tests, the herbicide is applied either as a surface application after planting the seeds or vegetative propagules or by incorporation into a quantity of soil to be applied as a cover layer over the test seeds in pre-seeded test containers. In the field tests, the herbicide is pre-plant incorporated ("P.P.I.") into the soil, i.e., the herbicide is applied to the surface of the soil, then incorporated therein by mixing means followed by planting of the crop seeds.

The surface application test method used in the greenhouse is performed as follows: containers, e.g., aluminum pans typically 9.5"×5.25"×2.75" (24.13 cm×13.34 cm×6.99 cm) or plastic pots 3.75"×3.75"×3" (9.53 cm×9.53 cm×7.62 cm) having drain holes in the bottom, are level-filled with Ray silt loam soil then compacted to a level 0.5 inch (1.27 cm) from the top of the pots. The pots are then seeded with a plant species to be tested, then covered with a 0.5 inch layer of the test soil. The herbicide is then applied to the surface of the soil with a belt sprayer at 20 gal/A, 30 psi (187 l/ha, 2.11 kg/cm$^2$); other sprayer means, e.g., a DeVilbiss sprayer, are also used on occasion. Each pot receives 0.25 inch (0.64 cm) water as overhead irrigation and the pots are then placed on greenhouse benches for subsequent sub-irrigation as needed. As an alternative procedure, the overhead irrigation may be omitted. Observations of herbicidal effects are made about three weeks after treatment.

The herbicide treatment by soil incorporation used in greenhouse tests are as follows:

A good grade of top soil was placed in aluminum pans and compacted to a depth of three-eighths to one-half inch from the top of the pan. On the top of the soil is placed a number of seeds or vegetative propagules of various plant species. The soil required to level fill the pans after seeding or adding vegetative propagules is weighed into a pan. The soil and a known amount of the active ingredient applied in a solvent or as a wettable powder suspension are thoroughly mixed, and used to cover the prepared pans. After treatment, the pans are given an initial overhead irrigation of water, equivalent to one-fourth inch (0.64 cm) rainfall, then watered by subirrigation as needed to give adequate moisture for germination and growth. As an alternative procedure, the overhead irrigation may be omitted. Observations are made about three weeks after seeding and treating.

In the tables below, data for compounds which had been tested in plural runs has been averaged from rates of application within the range of 0.07 to 2.24 kg/ha (0.125 to 2.0 lb/A).

In a first comparative test, preemergence herbicidal activity data are presented in Table IV comparing the relative efficacy of the compounds of Examples 1 and 5, representative compounds of this invention with relevant compounds of the prior art viz. Compounds A, B, D, F and G, as selective herbicides against particular weeds commonly associated with sorghum. The weeds used in the tests herein have the following abbreviations in the tables: redroot pigweed (RPW), seedling johnsongrass (SJG), shattercane (SC), white proso millet (WPM), barnyardgrass (BYG), large crabgrass (LCG), and yellow foxtail (YFT).

TABLE IV

| Compound | $GR_{15}$ Rate (Kg/Ha) Sorghum | $GR_{85}$ Rate (KG/Ha) | | | | | | | |
|---|---|---|---|---|---|---|---|---|---|
| | | RPW | SJG | LCG | SC | BYG | YNS | WPM | YFT |
| A | 0.28 | 2.24(NS) | <0.14(>2.0) | <0.14(>2.0) | 0.56(NS) | <0.14(>2.0) | 1.57(NS) | 1.12(NS) | <0.14(>2.0) |
| B | <0.14 | 0.28(NS) | <0.14(—) | <0.14(—) | 0.28(NS) | <0.14(—) | 1.12(NS) | 0.56(NS) | <0.14(—) |

TABLE IV-continued

| Compound | $GR_{15}$ Rate (Kg/Ha) Sorghum | $GR_{85}$ Rate (KG/Ha) | | | | | | | |
|---|---|---|---|---|---|---|---|---|---|
| | | RPW | SJG | LCG | SC | BYG | YNS | WPM | YFT |
| D | <0.14 | 0.28(NS) | <0.14(—) | <0.14(—) | <0.14(NS) | <0.14(—) | <0.14(NS) | 0.14(NS) | <0.14(—) |
| G | <0.14 | 0.28(NS) | <0.14(—) | <0.14(—) | 0.28(NS) | <0.14(—) | <0.14(—) | 0.56(NS) | <0.14(—) |
| F | <0.14 | 0.34(NS) | <0.14(—) | <0.14(—) | 0.14(NS) | <0.14(—) | 0.34(NS) | 0.56(NS) | 0.14(—) |
| Ex. 1 | 1.12 | >2.24(NS) | 0.14(8.0) | <0.14(>8.0) | 2.07(NS) | <0.14(>8.0) | 2.07(NS) | 1.68(NS) | <0.14(>8.0) |
| Ex. 5 | >2.24 | >2.24(—) | 0.14(>16.0) | <0.14(>16.0) | 2.24(>1.0) | 0.14(>16.0) | 1.46(>1.5) | >2.24(—) | 0.56(>4.0) |

Reference to the data in Table IV will show that, with respect to crop safety (as indicated by the $GR_{15}$ rate for sorghum), the invention compounds exhibited outstanding superiority vis-a-vis the prior art compounds. More particularly, with respect to the prior art compounds most closely-related in structure, i.e., compounds A and B having the N-alkoxymethyl-2'-alkoxy-6'-alkyl-2-haloacetanilide configuration, the invention compounds in the test were from at least 8.0 to greater than 16.0 times safer on sorghum than Compound B and from about 4.0 to greater than 8.0 times safer than Compound A. In like manner, the invention compounds were from 8.0 to more than 16 times safer on sorghum than homologous prior art Compounds D, F and G, each of which caused more than 15% injury to sorghum at the very low rate of less than 0.14 kg/ha.

With respect to weed control, indicated by the $GR_{85}$ application rates under each weed, it will be noted that all of the prior art compounds in the test, except Compound A, were either completely non-selective or questionably or marginally selective against all of the weeds in the test in sorghum. Compared with Compound A, the invention compounds were from about 4.0 to 8.0 times more effective against seedling johnsongrass, large crabgrass and barnyardgrass and 2.0 to 4.0 times as effective against yellow foxtail. The compound of Example 5 also exhibited positive selective control of shattercane and yellow nutsedge and marginal selectivity with respect to redroot pigweed and white proso millet where Compound A did not.

In another comparative test, the compound of Example 1 was compared for its preemergence herbicidal efficacy relative to that of Compounds C, D and J; data from this test is shown in Table V.

TABLE V

| Compound | $GR_{15}$ Rate (Kg/Ha) Sorghum | $GR_{85}$ Rate (Kg/Ha) | | | |
|---|---|---|---|---|---|
| | | SJG | BYG | LCG | YFT |
| D | <0.14 | 0.14(NS) | <0.14(—) | <0.14(—) | <0.14(—) |
| C | <0.14 | 0.28(NS) | <0.14(—) | <0.14(—) | <0.14(—) |
| J | <0.14 | 0.14(NS) | <0.14(—) | <0.14(—) | <0.14(—) |
| Ex. 1 | 1.12 | 0.84(1.3) | <0.14(>8.0) | <0.14(>8.0) | <0.14(>8.0) |

Referring to the data in Table V, it is noted that the invention compound of Example 1 had a substantially higher safety factor in sorghum than the prior art compounds, i.e., at least 8.0 times as safe. Moreover, in addition to possessing a higher crop safety factor, the invention compound exhibited uniformly and outstandingly superior selectivity factors than the prior art compounds against each of the weeds in the test. It will be noted that prior art Compounds C, D and J failed to exhibit positive crop selectivity against seedling johnsongrass and the selectivity of these compounds against the remaining weeds was questionable or marginal at best; in any event, the low safety factors of these compounds render them unsuitable as sorghum herbicides.

Additional preemergence herbicidal data from other tests for the compounds of Examples 1-8 are shown in Table VI.

In Table VI are shown the $GR_{15}$ and $GR_{85}$ rates for each invention compound in sorghum and the relevant weeds, respectively; selectivity factor values are shown in parenthesis. Data from multiple tests is represented as the average of the indicated number of tests. A blank space under a particular weed indicates that that weed was not present in the given test for the relevant compound.

TABLE VI

| Compound | $GR_{15}$ Rate (Kg/Ha) Sorghum | $GR_{85}$ Rate (KG/Ha) | | |
|---|---|---|---|---|
| | | RPW | SJG | LCG |
| Ex. 1[a] | 1.14 | >0.41(>2.8) | 0.43(2.7) | <0.09(>12.7) |
| Ex. 2 | >1.12 | | 0.56(>2.0) | <0.14(>8.0) |
| Ex. 3 | >1.12 | | 0.56(>2.0) | 0.28(>4.0) |
| Ex. 4[b] | 0.57 | 0.43(1.3) | <0.16(>3.6) | 0.09(>6.4) |
| Ex. 5[c] | >2.24 | >2.24(—) | 0.28(>8.0) | <0.12(>18.7) |
| Ex. 6[c] | 0.7 | 0.14(5.0) | 0.14(5.0) | <0.14(>5.0) |
| Ex. 7[d] | >0.7 | 0.35(>2.0) | <0.09(>7.8) | >0.11(~6.4) |
| Ex. 8 | >1.12 | | 0.21(>5.3) | 0.28(>4.0) |

| Compound | $GR_{85}$ Rate (KG/Ha) | | |
|---|---|---|---|
| | SC | BYG | YNS |
| Ex. 1[a] | 0.97(1.18) | 0.095(12.0) | 1.0(1.14) |
| Ex. 2 | | ~0.22(~5.0) | |
| Ex. 3 | | 0.28(>4.0) | |
| Ex. 4[b] | <0.15(>3.8) | <0.09(>6.4) | 0.35(1.6) |
| Ex. 5[c] | 1.3(>1.7) | 0.16(>14.0) | >1.9(~1.2) |
| Ex. 6[c] | 0.14(>5.0) | <0.11(>6.4) | 0.43(1.6) |
| Ex. 7[d] | <0.07(>10.0) | <0.09(>7.8) | 0.84(NS) |
| Ex. 8 | | 0.28(>4.0) | |

| Compound | $GR_{85}$ Rate (KG/Ha) | |
|---|---|---|
| | WPM | YFT |
| Ex. 1[a] | 0.75(1.52) | 0.12(9.5) |
| Ex. 2 | | 0.16(>7.0) |
| Ex. 3 | | 0.46(>2.4) |
| Ex. 4[b] | 0.64(NS) | 0.09(6.4) |
| Ex. 5[c] | >1.4(~1.6) | 0.36(>6.2) |
| Ex. 6[c] | 0.21(3.3) | <0.11(>6.4) |
| Ex. 7[d] | 0.21(>3.3) | <0.09(>7.8) |

TABLE VI-continued

| Ex. 8 | 0.28(>4.0) |

*aData represent average of seven replicate runs*
*bData represent average of five replicate runs*
*cData represent average of two replicate runs*
*dData represent average of three replicate runs*

Referring to the data in Table VI, it will be noted first that every invention compound tested against both seedling johnsongrass and shattercane selectivity controlled these weeds in sorghum at application rates within the range of 0.57–2.24 kg/ha; an accomplishment unmatched by any known prior art compound to the inventor's knowledge, including the commercial herbicides Compounds H and I—and Compound H is a leading commercial sorghum herbicide. Moreover, but for three exceptions, every invention compound exhibited positive selective control of every weed tested; the exceptions were the lack of positive selectivity of the compound of Example 4 against white proso millet and the compound of Example 7 against yellow nutsedge and the marginal selectivity of the compound of Example 5 against redroot pigweed.

Since the preemergence herbicidal data presented in Tables IV–VI were obtained according to identical routine procedures, a comparison of the herbicidal efficacy of the invention compounds in Table VI may also be made against the herbicidal efficacy for the prior art compounds in Tables IV and V. Here, again, it is clearly demonstrated that each of the invention compounds is outstandingly superior to all of the most relevant prior art compounds in terms of crop safety, without exception, and overall selective weed control as evidenced by selectivity factors; again, with exceptions in isolated cases. In more particular, of all the prior art compounds tested, only Compound A (Table IV) exhibited positive selective control of seedling johnsongrass, crabgrass, barnyardgrass and yellow foxtail in sorghum; Compound A was non-selective against the remaining weeds in the test. Against those weeds which Compound A did selectively control, the invention compounds exhibited outstandingly higher selectivity, with the exceptions of the compounds of Example 2 and 3 which performed comparably to Compound A against seedling johnsongrass. Again, in any event, the low sorghum safety factors and/or non-selectivity or questionable selectivity of the relevant prior art compounds against all weeds in the above tests render those compounds completely unsuitable as sorghum herbicides.

As mentioned earlier, Compounds H and I are referred to in prior art patents identified above and are the active ingredients in commercial herbicides; Compound H is widely used as a sorghum herbicide. Althought neither of these compounds are homologs, isomers or analogs of the invention compounds, these compounds were tested in the identical manner and against the same weeds used in the tests for the invention compounds as shown in Tables IV–VI in order to determine their preemergence herbicidal activity vis-a-vis the invention compounds. It was determined (based on averages of five replicate tests of Compound I and nine replicate tests with Compound H) that neither compound selectively controlled shattercane in sorghum and that Compound H exhibited no positive control of seedling johnsongrass, whereas Compound I exhibited only marginal selectivity, having a selectivity factor on the order of about 1.2 against seedling johnsongrass. Otherwise Compounds H and I did exhibit selective control of the remaining weeds shown in Tables IV-VI. Accordingly, it is apparent that the invention compounds provide marked advantages even relative to commercial herbicides in the selective control of weeds in sorghum.

The compounds of this invention have selective herbicidal activity in a variety of crops other than sorghum as indicated in Table III above. In yet other tests, the compound of Example 5 was also shown to be useful at rates in excess of 1.0 lb/A (1.12 kg/ha) in soybeans, field corn, cotton, cucumber, snap beans, garden peas, tomatoes and peanuts.

Therefore, it will be appreciated from the foregoing detailed description that compounds according to this invention have demonstrated unexpected and outstandingly superior herbicidal properties both absolutely and relative to the most structurally relevant compounds, other related homologs and analogs, including commercial 2-haloacetanilides of the prior art. More particularly, compounds of this invention have demonstrated outstanding crop safety in sorghum and selectivity factors particularly with respect to hard-to-kill weed species such as seedling johnsongrass and shattercane and other problem weeds such as redroot pigweed, yellow nutsedge, white proso millet, yellow foxtail, barnyardgrass, crabgrass, etc., as shown in Tables II–VI.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of aqueous suspension, preferably 480 to 600 g/l. The microencapsulation process referred to here is described in more detail in the assignee's copending U.S. Ser. No. 23,566 filed Mar. 26, 1979.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-S-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium Ureas N'-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea Carbamates/Thiolcarbamates 2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl]amino]-phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ monoalkyl amine and alkaline metal salts and combinations thereof

Ethers 2,4-Dichlorophenyl-4-nitrophenyl ether
2-Chloro-α,α,α-trifluoro-p-tolyl-3-ethoxy-4-nitrodiphenyl ether

Miscellaneous 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

|  | Weight Percent |
|---|---|
| I. Emulsifiable Concentrates | |
| A. Compound of Example No. 1 | 50.0 |
| Calcium dodecylbenzene sulfonate/polyoxyethylene ethers blend (e.g., Atlox ® 3437F and Atlox 3438F) | 5.0 |
| Monochlorobenzene | 45.0 |
| | 100.0 |
| B. Compound of Example No. 2 | 85.0 |
| Calcium dodecyl sulfonate/alkylaryl polyether alcohol blend | 4.0 |
| C₉ aromatic hydrocarbons solvent | 11.0 |
| | 100.00 |
| C. Compound of Example No. 3 | 5.0 |
| Calcium dodecylbenzene sulfonate/polyoxyethylene ethers blend (e.g., Atlox 3437F) | 1.0 |
| Xylene | 94.0 |
| | 100.00 |
| II. Liquid Concentrates | |
| A. Compound of Example No. 4 | 10.0 |
| Xylene | 90.0 |
| | 100.00 |
| B. Compound of Example No. 5 | 85.0 |
| Dimethyl sulfoxide | 15.0 |
| | 100.00 |
| C. Compound of Example No. 6 | 50.0 |
| N—methylpyrrolidone | 50.0 |
| | 100.00 |
| D. Compound of Example No. 7 | 5.0 |
| Ethoxylated castor oil | 20.0 |
| Rhodamine B | .5 |
| Dimethyl formamide | 74.5 |
| | 100.00 |
| III. Emulsions | |
| A. Compound of Example No. 8 | 40.0 |
| Polyoxyethylene/polyoxypropylene block copolymer with butanol (e.g., Tergitol ® XH) | 4.0 |
| Water | 56.0 |
| | 100.00 |
| B. Compound of Example No. 1 | 5.0 |
| Polyoxyethylene/polyoxypropylene block copolymer with butanol | 3.5 |
| Water | 91.5 |
| | 100.00 |
| IV Wettable Powders | |
| A. Compound of Example No. 3 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example No. 5 | 80.0 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 6 | 10.0 |
| Sodium lignosulfonate | 3.0 |
| Sodium N—methyl-N—oleyl-taurate | 1.0 |
| Kaolinite clay | 86.0 |
| | 100.00 |
| V. Dusts | |
| A. Compound of Example No. 3 | 2.0 |
| Attapulgite | 98.0 |
| | 100.00 |
| B. Compound of Example No. 4 | 60.0 |
| Montmorillonite | 40.0 |
| | 100.00 |
| C. Compound of Example No. 5 | 30.0 |
| Bentonite | 70.0 |
| | 100.00 |
| D. Compound of Example No. 6 | 1.0 |
| Diatomaceous earth | 99.0 |
| | 100.00 |
| VI. Granules | |
| A. Compound of Example No. 7 | 15.0 |
| Granular attapulgite (20/40 mesh) | 85.0 |
| | 100.00 |
| B. Compound of Example No. 8 | 30.0 |
| Diatomaceous earth (20/40) | 70.0 |
| | 100.00 |
| C. Compound of Example No. 1 | 0.5 |
| Bentonite (20/40) | 99.5 |
| | 100.00 |
| D. Compound of Example No. 2 | 5.0 |
| Pyrophyllite (20/40) | 95.0 |
| | 100.00 |
| VII. Microcapsules | |
| A. Compound of Example No. 4 encapsulated in polyurea shell wall | 49.2 |
| Sodium lignosulfonate (e.g. Reax 88 ® B) | 0.9 |
| Water | 49.9 |
| | 100.00 |
| B. Compound of Example No. 5 encapsulated in polyurea shell wall | 10.0 |
| Potassium lignosulfonate (e.g., Reax ® C-21) | .5 |
| Water | 89.5 |
| | 100.00 |
| C. Compound of Example No. 6 encapsulated in polyurea shell wall | 80.0 |
| Magnesium salt of lignosulfate (Treax, LTM ®) | 2.0 |
| Water | 18.0 |
| | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

What is claimed is:

1. Compounds of the formula

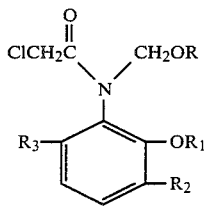

wherein
  R is isopropyl, n-butyl, isobutyl, sec-butyl, allyl or 2-methylbutyl;
  $R_1$ is methyl, isopropyl, n-butyl or allyl and
  $R_2$ and $R_3$ are hydrogen or methyl; provided that;
  $R_1$, $R_2$ and $R_3$ are each methyl when R is n-butyl, isobutyl or sec-butyl;
  $R_2$ and $R_3$ are each hydrogen when R is isopropyl, isobutyl or sec-butyl and $R_1$ is isopropyl or n-butyl and
  $R_2$ is hydrogen and $R_3$ is methyl when R is 2-methylbutyl or allyl and $R_1$ is allyl.

2. Compound according to claim 1 which is N-(isobutoxymethyl)-2'-methoxy-3',6'-dimethyl-2-chloroacetanilide.

3. Compound according to claim 1 which is N-(n-butoxymethyl)-2'-methoxy-3',6'-dimethyl-2-chloroacetanilide.

4. Compound according to claim 1 which is N-(sec-butoxymethyl)-2'-methoxy-3',6'-dimethyl-2-chloroacetanilide.

5. Compound according to claim 1 which is N-(allyloxymethyl)-2'-allyloxy-6'-methyl-2-chloroacetanilide.

6. Compound according to claim 1 which is N-(2-methylbutoxymethyl)-2'-allyl-6'-methyl-2-chloroacetanilide.

7. Compound according to claim 1 which is N-(isopropoxymethyl)-2'-isopropoxy-2-chloroacetanilide.

8. Compound according to claim 1 which is N-(isobutoxymethyl)-2'-isopropoxy-2-chloroacetanilide.

9. Compound according to claim 1 which is N-(sec-butoxymethyl)-2'-n-butoxy-2-chloroacetanilide.

10. Herbicidal compositions comprising an adjuvant and a herbicidally effective amount of a compound having the formula

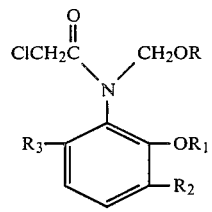

wherein
  R is isopropyl, n-butyl, isobutyl, sec-butyl, allyl or 2-methylbutyl;
  $R_1$ is methyl, isopropyl, n-butyl or allyl and
  $R_2$ and $R_3$ are hydrogen or methyl; provided that;
  $R_1$, $R_2$ and $R_3$ are each methyl when R is n-butyl, isobutyl or sec-butyl;
  $R_2$ and $R_3$ are each hydrogen when R is isopropyl, isobutyl or sec-butyl and $R_1$ is isopropyl or n-butyl and
  $R_2$ is hydrogen and $R_3$ is methyl when R is 2-methylbutyl or allyl and $R_1$ is allyl.

11. Composition according to claim 10 wherein said compound is N-(isobutoxymethyl)-2'-methoxy-3',6'-dimethyl-2-chloroacetanilide.

12. Composition according to claim 10 wherein said compound is N-(n-butoxymethyl)-2'-methoxy-3',6'-dimethyl-2-chloroacetanilide.

13. Composition according to claim 10 wherein said compound is N-(sec-butoxymethyl)-2'-methoxy-3',6'-dimethyl-2-chloroacetanilide.

14. Composition according to claim 10 wherein said compound is N-(allyloxymethyl)-2'-allyloxy-6'-methyl-2-chloroacetanilide.

15. Composition according to claim 10 wherein said compound is N-(2-methylbutoxymethyl)-2'-allyl-6'-methyl-2-chloroacetanilide.

16. Composition according to claim 10 wherein said compound is N-(isopropoxymethyl)-2'-isopropoxy-2-chloroacetanilide.

17. Composition according to claim 10 wherein said compound is N-(isobutoxymethyl)-2'-isopropoxy-2-chloroacetanilide.

18. Composition according to claim 10 wherein said compound is N-(sec-butoxymethyl)-2'-n-butoxy-2-chloroacetanilide.

19. Method for combatting undesirable plants associated with sorghum which comprises applying to the locus of said plants a herbicidally effective amount of a compound of the formula

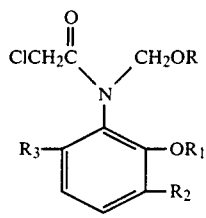

wherein
- R is isopropyl, n-butyl, isobutyl, sec-butyl, allyl or 2-methylbutyl;
- $R_1$ is methyl, isopropyl, n-butyl or allyl and
- $R_2$ and $R_3$ are hydrogen or methyl; provided that;
- $R_1$, $R_2$ and $R_3$ are each methyl when R is n-butyl, isobutyl or sec-butyl;
- $R_2$ and $R_3$ are each hydrogen when R is isopropyl, isobutyl or sec-butyl and $R_1$ is isopropyl or n-butyl and
- $R_2$ is hydrogen and $R_3$ is methyl when R is 2-methylbutyl or allyl and $R_1$ is allyl.

20. Method according to claim 19 wherein said compound is N-(isobutoxymethyl)-2'-methoxy-3',6'-dimethyl-2-chloroacetanilide.

21. Method according to claim 19 said compound is N-(n-butoxymethyl)-2'-methoxy-3',6'-dimethyl-2-chloroacetanilide.

22. Method according to claim 19 wherein said compound is N-(sec-butoxymethyl)-2'-methoxy-3',6'-dimethyl-2-chloroacetanilide.

23. Method according to claim 19 wherein said compound is N-(allyloxymethyl)-2'-allyloxy-6'-methyl-2-chloroacetanilide.

24. Method according to claim 19 wherein said compound is N-(2-methylbutoxymethyl)-2'-allyl-6'-methyl-2-chloroacetanilide.

25. Method according to claim 19 wherein said compound is N-(isopropoxymethyl)-2'-isopropoxy-2-chloro-acetanilide.

26. Method according to claim 19 wherein said compound is N-(isobutoxymethyl)-2'-isopropoxy-2-chloroacetanilide.

27. Method according to claim 19 wherein said compound is N-(sec-butoxymethyl)-2'-n-butoxy-2-chloroacetanilide.

* * * * *